United States Patent [19]

Matt et al.

[11] 4,088,678

[45] May 9, 1978

[54] SUBSTITUTED SUCCINIC ACID COMPOUNDS AND THEIR USE AS CHELANTS

[75] Inventors: Joseph Matt, Downers Grove; Manuel Slovinsky, Woodridge, both of Ill.

[73] Assignee: Nalco Chemical Company, Oak Brook, Ill.

[21] Appl. No.: 701,785

[22] Filed: Jul. 1, 1976

[51] Int. Cl.² .......................... C07F 9/30; C02B 5/06
[52] U.S. Cl. .............................. 260/502.4 R; 210/58; 252/180; 260/501.19; 260/501.2; 260/501.21
[58] Field of Search ............... 260/502.4 R, 501.19, 260/501.2, 501.21

[56] References Cited

U.S. PATENT DOCUMENTS

| | | | |
|---|---|---|---|
| 2,957,931 | 10/1960 | Hamilton et al. | 260/502.4 R |
| 3,160,632 | 12/1964 | Toy et al. | 260/502.5 |
| 3,236,863 | 2/1966 | Smith et al. | 260/502.4 R |
| 3,886,204 | 5/1975 | Geffers et al. | 260/502.4 R |
| 3,886,205 | 5/1975 | Geffers et al. | 260/502.4 R |
| 3,923,876 | 12/1975 | Heins et al. | 260/502.4 R |
| 3,933,427 | 1/1976 | Bohnsack et al. | 260/502.4 R |
| 4,020,101 | 4/1977 | Geffers et al. | 260/502.4 R |

OTHER PUBLICATIONS

Pudovik, "Bull. Acad. Sci. U.S.S.R. (English translation), (1952), pp. 821–824.
Imaev et al., "Chemical Abstracts", vol. 79, (1973), 53557z.
Pudovik et al., "Chemical Abstracts", vol. 54, (1960), col. 15223.

*Primary Examiner*—Joseph E. Evans
*Attorney, Agent, or Firm*—John G. Premo; Robert A. Miller; Barry W. Sufrin

[57] ABSTRACT

Substituted succinic acids and salts thereof having the formula:

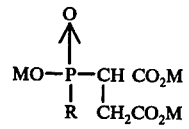

where R is H or

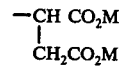

and M is H, alkali metal, or an amine, are useful as chelants and stabilizers for heavy metal ions.

1 Claim, No Drawings

SUBSTITUTED SUCCINIC ACID COMPOUNDS AND THEIR USE AS CHELANTS

This invention relates to substituted succinic acids and salts thereof which have the structural formula:

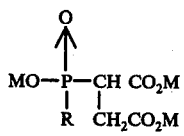

In the above formula, R is H or

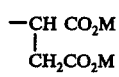

and M is H, alkali metal, ammonia or an amine.

R in preferred compositions of the invention is:

The synthesis of these substituted succinic acids and their salts is readily accomplished by reacting an aqueous solution of maleic acid or its anhydride or salts, with an alkali metal hypophosphite at a temperature of about 60° C. for 6 hours using a free radical initiator such as ammonium persulfate. This method of preparing these compunds forms no part of this invention.

The reaction of certain maleic acid derivatives with hypophosphites to produce substituted succinic acid derivatives has previously been reported in the literature. These compounds are not the same compounds as are disclosed and claimed herein.

In Chemical Abstracts 1975, 125, 447, it is shown that sodium hypophosphite and monoalkyl maleates may be fused to ostensibly product a substitute monosuccinate ester of hypophosphorous acid. Neither the free succinic acid nor its salts are disclosed as being produced by the reaction.

In Russian Pat. No. 376,388 (Chemical Abstracts Volume 79;53557z), sodium hypophosphite is reacted with a C$_{12}$ alcohol ester of maleic acid. Neither the free succinic acid nor its salts are disclosed.

In Chemical Abstracts Volume 54;15,223, ethyl maleate is reacted with sodium hypophosphite to produce an ethyl succinate derivative of the hypophosphorous acid but the free succinic acid is not formed during the course of the reaction procedures described in this reference.

None of the above references disclose the specific preferred composition of the invention,

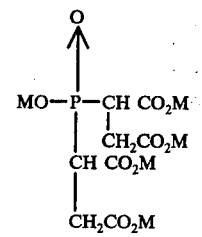

where M has the values previously disclosed.

The compositions of the invention are useful in treating hardness-containing waters to prevent the hardness-imparting metals, e.g., calcium, magnesium or iron, from forming scale or tenaciously adhering deposits.

The compositions of the invention are capable of operating upon hardness-containing waters to the extent that as little as a few parts per million will effectively prevent calcium from either precipitating or will modify the nature of calcium-containing pecipitates so that they are rendered substantially non-adherent to metallic surfaces of the type found in industrial apparatus, such as cooling towers, boilers, heat exchangers, and the like. While the compositions of the invention operate at a low dosage, they are also capable of acting to stoichiometrically combine with the hardness-forming ions in water to render them non scale-forming.

EXAMPLES

To illustrate the invention, the following are presented by way of example:

Preparation of Sodium phosphinico bis succinate

Maleic acid 25.5g, 0.22m) was dissolved in 30 gm. of H$_2$O, and sodium hypophosphite monohydrate (11.33g 0.11m) was added. At 60° C., the solution was treated over 4 hours with small portions of ammonium persulfate (1.9g in all). Heating was continued 2 hours more. The solution contained monosodium phosphinico succinate. Infra-red and NMR examination showed disappearance of the maleic double bond, indicating complete adduction.

Using the above described preparative techniques, several other substituted succinates were prepared. The results of these preparations are set forth in Table 1.

TABLE 1

| Number | Maleate | Hypophosphite | Ratio | Time, hrs | Temp. °C | Mole % Cat. (on actives) | Other Conditions | Ca Chelation mg. CaCO$_3$/g |
|---|---|---|---|---|---|---|---|---|
| 1 | H$_2$ | Na | 2.2/1 | 6 | 60 | 2.5 | | 338 |
| 2 | H$_2$ | Na | 2.2/1 | 6 | 60 | 2.5 | 10% less H$_2$O | 188 |
| 3 | H$_2$ | Na | 2.2/1 | 6 | 60 | 2.5 | N$_2$ | 300 |
| 4 | Na$_2$ | Na | 2.0/1 | 6 | 60 | 2.5 | | 260 |
| 5 | H$_2$ | H | 2.0/1 | 6 | 60 | 2.5 | N$_2$ | |
| 6 | H$_2$ | H | 1.2/1 | 6 | 60 | 2.5 | — | — |

In the last column of Table 1 it is noted that calcium chelation values are given for the various materials that were prepared. This total chelation value is determined by titrating with a solution of calcium chloride in the presence of oxalate at a pH of 10.5 or slightly higher. The chelating agent will complex the calcium until an excess of calcium is present. A white calcium oxalate precipitate indicates the end point of the titration. Table 1 illustrates the results obtained using the following method.

I. Reagents
  A. Ammonium oxalate, saturated solution:

Dissolve 60 grams of ACS reagent grade (calcium free) ammonium oxalate in a liter of hot water and allow to cool to room temperature.

B. Calcium chloride, standard solution:

Dissolve 50.05g. of primary calcium carbonate in 300 mls of distilled water by slowly adding 86 mls of hydrochloric acid to completely dissolve the carbonate. Heat to boiling and then cool to room temperature. Neutralize the excess acid with ammonium hydroxide until slightly alkaline to litmus and dilute the solution to exactly one liter in a volumetric flask. Dilute 100 mls of this primary solution to one liter and use as the titrating solution.

C. Ammonium hydroxide, concentrated reagent.
D. Hydrochloric acid, concentrated reagent.

II. Procedure

A. Weight 10.00 grams of a 15% toluene solution of a maleic anhydride vinyl acetate (1:1) copolymer and dilute to 500 mls in a volumetric flask using distilled water.

B. Pipette 25 mls of this solution into a clean 250 ml Erlenmeyer flask.

C. Add 60 mls of distilled water.

D. Add 1 ml of saturated ammonium oxalate solution.

E. Titrate the sample to the first permanent turbidity with the diluted calcium chloride solution. Check the pH of the system and, if less than 10.5, adjust with ammonium hydroxide. Complete the titration if the precipitate has dissolved. Care should be taken to avoid over titration since the end point is not sharp.

III. Calculation $$\frac{(\text{ml CaCl}_2 \text{ solution})}{0.5} \times 5 = \text{mg. CaCO}_3/\text{gram of chelating agent} = \text{chelation value}$$

To demonstrate the accuracy of the above described test methods, it was used to determine the chelation value of the well-known chelants: ethylene diamine tetraacetic acid (EDTA) and nitriloacetic acid, (NTA). In the case of EDTA, the experimental value was 255 with the calculated value being 255. In the case of NTA, the experimental value was 350 whereas the calculated value was 360.

It, therefore, becomes evident that the substituted bis succinic acids of the invention are chelating agents.

Composition 1, Table 1, was prepared as a dilute aqueous solution and divided into several aliquot portions. To the solutions were added varying amounts of standard alkalies including sodium hydroxide, potassium hydroxide, ammonium hydroxide, triethanol amine, ethylene diamine and diethyl amine. The amounts of these alkalies were calculated so as to convert the active hydrogen of the succinic acid portion of the molecule into its corresponding salts.

CONCLUSION

It is evident that the invenion provides new and useful substituted succinic acids and salts thereof which are readily prepared from aqueous solutions of sodium hypophosphite using mild reaction conditions and relatively short reaction times. The products of the invention are water-soluble and are readily capable of being formulated with a variety of known water treating agents such as lignins, water-soluble polymers, e.g. polyacrylic acid salts and the like, to produce finished products having a wide range of utility in the water treating arts.

Having thus described our invention, it is claimed as follows:

1. Substituted succinic acids and salts thereof having the formula:

where M is H, alkali metal, ammonia or amine and R is:

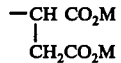

* * * * *